(12) United States Patent
Bernhardt et al.

(10) Patent No.: US 9,545,234 B2
(45) Date of Patent: Jan. 17, 2017

(54) METHOD FOR OBTAINING IMAGE DATA WITH THE AID OF AN X-RAY IMAGE RECORDING APPARATUS HAVING A FILTER AND AN X-RAY IMAGE RECORDING APPARATUS

(75) Inventors: Philipp Bernhardt, Forchheim (DE); Stefan Böhm, Oberasbach (DE); Richard Obler, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 840 days.

(21) Appl. No.: 13/477,092

(22) Filed: May 22, 2012

(65) Prior Publication Data

US 2012/0300905 A1    Nov. 29, 2012

(30) Foreign Application Priority Data

May 24, 2011    (DE) .................. 10 2011 076 371

(51) Int. Cl.
*G21K 5/04*    (2006.01)
*A61B 6/00*    (2006.01)

(52) U.S. Cl.
CPC .............. *A61B 6/4035* (2013.01); *A61B 6/542* (2013.01); *A61B 6/58* (2013.01)

(58) Field of Classification Search
CPC ....... A61B 6/545; A61B 6/405; A61B 6/4035; A61B 6/469; A61B 6/542; A61B 6/58; G21K 1/046; G21K 5/04; G06T 5/40; G06T 2207/20021; H04L 1/0001
USPC ....................................................... 378/62
See application file for complete search history.

(56) References Cited

U.S. PATENT DOCUMENTS

| | | | |
|---|---|---|---|
| 5,054,048 A * | 10/1991 | Wang ............................ | 378/146 |
| 7,630,477 B2 | 12/2009 | Hsieh | |
| 7,706,508 B2 | 4/2010 | Arenson | |
| 2001/0050974 A1* | 12/2001 | Schmitz ........................ | 378/159 |
| 2005/0089146 A1 | 4/2005 | Toth et al. | |
| 2008/0056608 A1* | 3/2008 | Spahn .......................... | 382/275 |
| 2008/0175462 A1 | 7/2008 | Bohm | |
| 2008/0232542 A1 | 9/2008 | Lin | |
| 2010/0308229 A1* | 12/2010 | Bertram et al. ......... | 250/363.04 |

FOREIGN PATENT DOCUMENTS

| | | |
|---|---|---|
| CN | 1611190 A | 4/2005 |
| CN | 1942141 A | 4/2007 |
| DE | 102008034580 A1 * | 2/2010 |
| WO | WO 2010128431 A1 * | 11/2010 |

OTHER PUBLICATIONS

Ikeda et al., Development and Evaluation of a Digital Radiography System using a Large-Area Flat Panel Detector, 2003, SPIE, vol. 5030, pp. 215-225.*
Translation of DE102008034580A1.*

* cited by examiner

*Primary Examiner* — David J Makiya
*Assistant Examiner* — John Corbett

(57) ABSTRACT

A method to optimally set a position of a form filter in an x-ray image recording apparatus is proposed. The x-ray image recording apparatus has an x-ray radiation source and an x-ray radiation detector. An x-ray image is firstly recorded in a first position of the form filter. A new position of the filter is then calculated and automatically set with the aid of the x-ray image. A new x-ray image is then recorded. With a minimal dose of a patient, the method enables low contrast images to be recorded for a minimal main dose of the patient, in particular in a sequence.

9 Claims, 2 Drawing Sheets

METHOD FOR OBTAINING IMAGE DATA WITH THE AID OF AN X-RAY IMAGE RECORDING APPARATUS HAVING A FILTER AND AN X-RAY IMAGE RECORDING APPARATUS

CROSS REFERENCE TO RELATED APPLICATIONS

This application claims priority of German application No. 10 2011 076 371.6 filed May 24, 2011, which is incorporated by reference herein in its entirety.

FIELD OF INVENTION

The invention relates to a method for obtaining image data relating to an image object with the aid of an x-ray radiation source and an x-ray radiation detector. The invention also relates to an x-ray image recording apparatus.

BACKGROUND OF INVENTION

Form filters are used to prevent massive contrasts in the image signal due to radiation protection and image quality. A form filter is a semi-transparent filter which absorbs more x-ray radiation in the beam path upstream of relatively x-ray transparent body areas like for instance the lungs and/or object parts but absorbs less x-ray radiation in the beam path upstream of body areas which themselves absorb relatively large quantities of the x-ray radiation, for instance bones. If applicable, a region of the form filter is also used to attenuate direct radiation, in other words such x-rays which do not penetrate the image object but instead run adjacent thereto at the edge for instance and reach the x-ray radiation detector.

Conventionally form filters were previously positioned purely manually. Alternatively, positioning with the aid of presaved positions is conventional. A manual re-positioning of the semitransparent filters is necessary particularly when recording parameters are changed, e.g. the acceleration voltage with respect to the x-ray radiation source or the image enlargement etc. Such a re-positioning is frequently not implemented due to lack of time. If applicable, a low-grade image quality is achieved as a result and the image object obtains an excessive x-ray radiation dose.

The technique of recording an x-ray image of the image object, detecting contrast-rich edges and positioning the filter along these edges also exists in the prior art.

This is disadvantageous in that a relatively high x-ray radiation dose is applied to the image object solely for the test image.

SUMMARY OF INVENTION

It is the object of the present invention to indicate a way in which a filter can be better or more reliably positioned than previously.

The object is achieved in one aspect by a method and in another aspect by an x-ray image recording apparatus having the features according to the claims. A filter is positioned between the x-ray radiation source and the image object, said filter filtering x-rays differently in different of its regions. Such a filter is also known as a form filter and can be moved into different positions in a motor-driven fashion.

In the inventive method, image data is obtained in a first position of the filter in which it filters part of the x-rays and a new position for the filter is calculated with the aid of the thus obtained image data. The filter is positioned in the new position and image data is obtained again.

The invention is based on the knowledge that a new position of the filter can also be defined with the aid of image data, in which the x-rays have already been filtered with the aid of the filter, and in particular an optimal position can also be determined. As a result of the filter filtering a part of the x-rays when obtaining the initially recorded image data of the filters, it is possible not to expose the image object to an excessively high dose of x-ray radiation. As a result of the position of the filter being determined with the aid of the image data, it is possible for the newly calculated position to be the most favorable according to a specific criterion.

In a preferred embodiment of the inventive method, this is continuously implemented, wherein the preceding new position becomes the new first position of the filter in each instance. The respective new position of the filter is calculated from the image data obtained last in each instance. The invention can in this way very quickly allow for changes in the conditions, be they in the image object itself, in the recording parameters, i.e. the filter position is currently adjusted in each instance. On account of specific constant settings, this does not result in negative effects like an excessive dose being administered to the patient or a low-grade image quality.

In a preferred aspect of the invention, the new position is the position in each instance in which a predetermined variable fulfills a predetermined criterion. In other words, a specific measure can be specified which provides information as to how good the respective position is and the optimal position can be selected.

For instance, the predetermined variable can be a measure of dispersion (preferably related to all image data) for data values of the image data. This may in particular be a variance which is minimal according to the predetermined criterion; it is precisely also possible to minimize the average deviation from the average value into the image data values.

A measure of scale should essentially be as minimal as possible. The smallness of the measure of scale is precisely the objective of the form filtering. Excessively high contrasts are to be avoided and approximately the same attenuation should be achieved after radiation passes through different regions of the image object in each instance.

In an alternative embodiment, the predetermined variable is a dose determined with the aid of image recognition with respect to a mapped structure, which dose is then to be minimal in accordance with the predetermined criterion. For instance, the main dose of the patient can be minimized at least approximately by suitably selecting the predetermined criterion. For instance, by the contours of the patient's body being identified with the aid of image recognition and thus the size of the irradiated surface of the skin being detected, it is then possible to determine the main dose of the patient overall by adding the main dose to individual surface elements by taking the effect of the filter into account in the respective position.

If a predetermined variable is to fulfill a predetermined criterion, then a calculation must be made to determine how this variable appears in the respective position. To this end it is helpful if the effect of the filter is initially calculated from the image data in the first position (in other words referring back to the situation without the filter). Then the effect of the filter can conversely be calculated again, nevertheless now for different positions of the filter, in particular also for positions which differ from the first position. The predetermined variable is determined in each instance.

The inventive x-ray image recording apparatus having an x-ray radiation source and an x-ray radiation detector as well as a (form) filter, which can be moved into different positions in a motor-driven manner, comprises a control facility, which is designed to automatically set a position of the filter with the aid of x-ray image data. The invention relates to the knowledge that only the x-ray image data are to be evaluated with the aid of an algorithm in order to find the best position of the filter with respect to the current situation in each instance.

The control facility is preferably designed to determine and set the position of the filter for the subsequent image recording from x-ray image data of an x-ray image recording obtained with the filter in each instance. In other words, the position of the filter is automatically updated by the x-ray image recording apparatus during each x-ray image recording, so that the operating personal is relieved of performing corresponding settings and there is no risk of such a setting not happening because there is no time available therefor.

The x-ray image recording apparatus preferably includes an x-ray radiation detector having a planar surface and the filter can be moved in at least in one direction in such a plane, which is parallel to the planar surface. This is the typical adjustment direction for a form filter, as is optimal to realize the x-ray image recording apparatus and in particular to implement the inventive method.

BRIEF DESCRIPTION OF THE DRAWINGS

A preferred embodiment of the invention is subsequently described in more detail with reference to the drawing, in which.

DETAILED DESCRIPTION OF INVENTION

Figure 1:
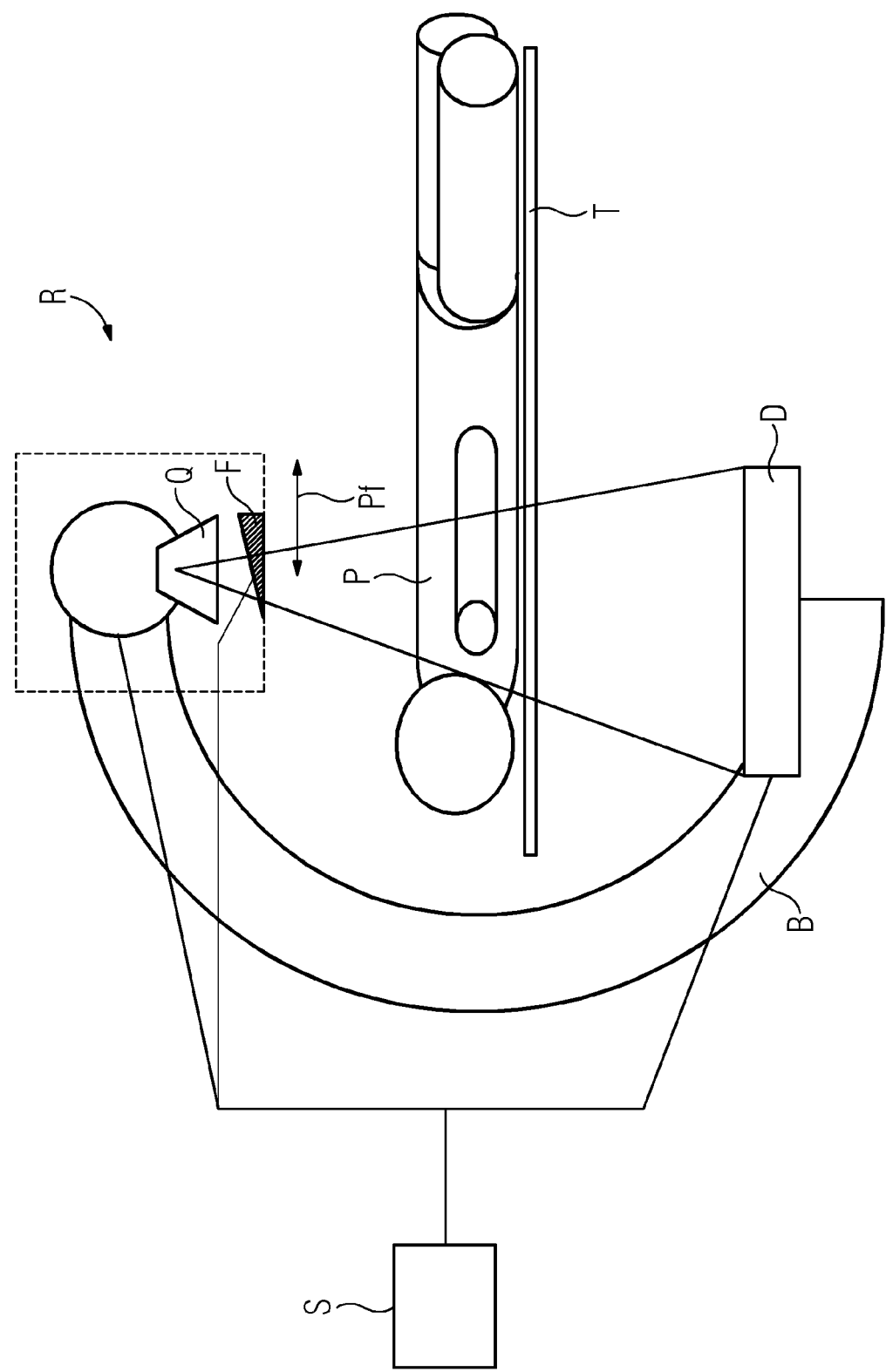
FIG. 1 shows an x-ray image recording apparatus, in which the invention can be implemented.
Figure 2:
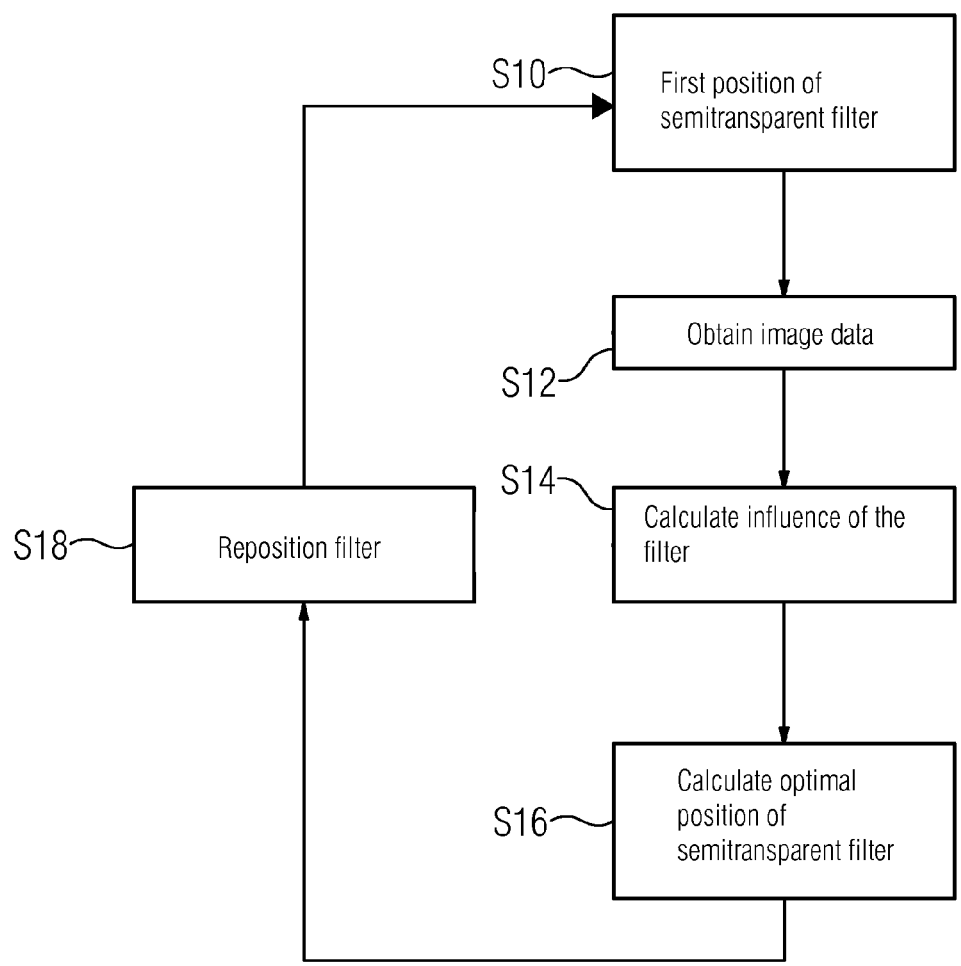
FIG. 2 shows a flow chart to explain an embodiment of the inventive method.

In an x-ray image recording apparatus which is referred to overall with R and can be embodied for instance in the manner of an x-ray angiography system, a patient P resting on a patient couch T as the image object is irradiated by x-rays, which emanate from an x-ray radiation source Q and strike an x-ray radiation detector D after passing through the patient P. The x-ray radiation source Q and the x-ray radiation detector D are arranged on an x-ray C-arm B and are controlled by a control facility S. In the radiation path between the x-ray radiation source Q and the patient P, a form filter F exists, which is shown wedge-shaped in FIG. 1. Motors which are not shown in the Figure are currently to be able to displace the filter F according to arrow Pf into a plurality of positions, wherein either on account of control commands to the motors by the control facility S or with the aid of positions sensors, which are not shown in FIG. 1, the position of the form filter F is known, i.e. is available as data in the control facility S.

The method begins in that a first position is initially assumed in step S10 for the form filter F (the semitransparent filter). An x-ray image is now recorded in step S12, i.e. image data is obtained with the aid of the x-ray radiation detector D, if the x-ray radiation source Q emits x-rays.

Since the filter F in the first position attenuates at least part of the x-ray radiation, the influence of the filter is calculated from the obtained 2D image data record in step S14, i.e. is corrected. An image data record as it would exist without a filter is therefore obtained. The advantage consists in this image data record not being directly obtained through image recording, thereby preventing the patient P from receiving an excessively large dose.

Since an x-ray image is now available without a filter, it is possible to calculate how the x-ray images appear if the filter F assumes different positions. With this calculation, it is possible to consider that on account of an automatic regulation and thus adjustment of the x-ray radiation dose by the control facility S, the x-ray radiation dose emitted by the x-ray radiation source Q is different in different positions of the semitransparent filter F.

A 2D image data record is thus obtained at each position of the filter F and a specific variable can be extracted from these 2D image data records. For instance, it is possible to determine the value of the variance in the data values (gray-scale values) of the 2D image data record in the respective position of the semitransparent filter F. The position which is the optimal position on account of the calculations is then selected, see step S16.

As an alternative to using a measure of scale like the variance, it is also possible to determine the contours of the patient P in the obtained x-ray image with the aid of image recognition and to derive therefrom the main dose of the patient for different positions of the form filter F in each instance. For instance, closed contours can be filled in each instance and surface elements within these closed contours are assigned values for the main dose, which are then added up as a whole. The position of the form filter F can also be found out here, similarly preferably by considering a corresponding dose adjustment by the control facility S, in which the variable used, currently therefore the main dose of the patient P, is minimal.

In both variants, the optimal position for the semi-transparent filter F is finally obtained in step S16.

In step S18, the filter F is then repositioned, namely moved precisely into the optimal position.

Image data is now obtained in step S12. Provided the method is not to end here, step S14 is implemented once again, a new optimal position is calculated once again in step S16 and if necessary the filter F is repositioned once again in step S18, so that new image data can be continuously obtained and each time the loop from steps S14, S16 and S18 is passed through so that the filter F has the current position in each instance which is optimally attuned to the current situation, both with respect both to the patient P and also to the setting parameters of the x-ray image recording apparatus, so that the variable used is minimal. Either the optimal image quality is obtained with the aid of the form filter F or provision is made for a minimal main dose of the patient P.

Aside from the use of a measure of scale for calculating the optimal position in step S16 using the (main) dose, other types of predetermined variables are also conceivable, which are used in step S16. The predetermined variable can finally also be composed of a plurality of individual variables, for instance both a measure of scale and also a (main) dose can be taken into account equally in the predetermined variable with the aid of suitable weights.

The invention claimed is:
1. A method for obtaining image data of an image object using an x-ray image recording apparatus having an x-ray radiation source and an x-ray radiation detector, comprising:
positioning a filter between the x-ray radiation source and the image object in a first position, the filter differently filtering x-rays from the x-ray radiation source in different regions of the filter;
obtaining a first image data of the image object at the first position by the x-ray image recording apparatus;
calculating an effect of the filter at the first position from the first obtained image data;
correcting the effect of the filter at the first position in the first obtained image data to obtain a corrected image data record;
calculating image data records with the filter at different assumed positions respectively based on the corrected image data record;
determining a dose adjustment of the x-rays with the filter at each of the respective different assumed positions;
determining a value of a variable from each of the image data records with the filter at each of the respective different assumed positions;
selecting an optimal position from the assumed different positions in which the value of the variable fulfills a predetermined criterion,
wherein the predetermined criterion specifies that the value of the variable is a minimal value in the optimal position,
wherein the optimal position is selected by taking into account the dose adjustment.

2. The method as claimed in claim 1, wherein the method steps are continuously implemented with the optimal position as a new first position.

3. The method as claimed in claim 1, wherein the variable is a variance of a measure of scale for data values of the each of the image data records with the filter at the each of the respective different assumed positions.

4. The method as claimed in claim 1, wherein the variable is an average deviation from an average value of data values of the image data records with the filter at the respective different assumed positions.

5. The method as claimed in claim 1, wherein the variable is a main dose for the different assumed positions and is determined by image recognition in the obtained first image data of the image object with respect to a mapped structure.

6. An x-ray image recording apparatus for obtaining image data of an image object, comprising:
an x-ray radiation source;
an x-ray radiation detector;
a filter positioned between the x-ray radiation source and the image object that can be moved into different positions; and
a control device that is configured to:
calculate an effect of the filter at a first position from a first x-ray image data obtained at the first position;
correct the effect of the filter at the first position in the first obtained image data to obtain a corrected image data record;
calculate image data records with the filter at different assumed positions respectively based on the corrected image data record;
determine a value of a variable from each of the image data records with the filter at each of the respective assumed positions; and
select an optimal position from the different assumed positions in which the value of the variable fulfills a predetermined criterion;
determine a dose adjustment of the x-rays with the filter at each of the respective different assumed positions; and
automatically set the filter to the optimal position,
wherein the predetermined criterion specifies that the value of the variable is a minimal value in the optimal position,
wherein the optimal position is selected by taking into account the dose adjustment.

7. The x-ray image recording apparatus as claimed in claim 6, wherein the control device is configured to continuously implement the steps with the optimal position as a new first position.

8. The x-ray image recording apparatus as claimed in claim 6, wherein the x-ray radiation detector comprises a planar surface, and wherein the filter can be moved in at least one direction in a plane that is parallel to the planar surface.

9. The x-ray image recording apparatus as claimed in claim 6, wherein the filter is moved by a motor.

* * * * *